US00PP29679P3

(12) United States Plant Patent
Ciccolella

(10) Patent No.: US PP29,679 P3
(45) Date of Patent: Sep. 18, 2018

(54) ***ACMENA* PLANT NAMED 'VICLOW'**

(50) Latin Name: *Acmena smithii*
Varietal Denomination: VICLOW

(71) Applicant: Vic Ciccolella, Oakville (AU)

(72) Inventor: Vic Ciccolella, Oakville (AU)

( * ) Notice: Subject to any disclaimer, the term of this patent is extended or adjusted under 35 U.S.C. 154(b) by 0 days.

(21) Appl. No.: 15/530,330

(22) Filed: Dec. 23, 2016

(65) Prior Publication Data

US 2018/0184557 P1 Jun. 28, 2018

(51) Int. Cl.
*A01H 5/00* (2018.01)
*A01H 5/12* (2018.01)

(52) U.S. Cl.
USPC ..... Plt./226
CPC ..... *A01H 5/12* (2013.01)

(58) Field of Classification Search
USPC ..... Plt./263.1, 226
See application file for complete search history.

(56) References Cited

PUBLICATIONS http://www.plantmark.com.au/acmena-low-n-leafy-30cm#. Nov. 28, 2015.*

* cited by examiner

*Primary Examiner* — Annette H Para
(74) *Attorney, Agent, or Firm* — Cassandra Bright

(57) ABSTRACT

A new and distinct *Acmena* cultivar named 'VICLOW' is disclosed, characterized by short, compact bushy plants. Plants have attractive new growth and foliage colored near greyed-orange. The new variety is a *Acmena* normally produced as an outdoor garden or container plant.

4 Drawing Sheets

Latin name of the genus and species: *Acmena smithii.*
Variety denomination: 'VICLOW'.

BACKGROUND OF THE INVENTION

The present invention comprises a new and distinct variety of *Acmena*, hereinafter referred to by the cultivar name 'VICLOW'. This new *Acmena* was developed through a breeding program in New South Wales, Australia. 'VICLOW' was selected from a population of seedlings grown from seed resulting from the open pollination of a group of unnamed, unpatented *Acmena smithii* plants. The open pollination resulting in the new variety was conducted during 2005. Selection of the new variety was made during 1997.

The first asexual propagation of 'VICLOW' was carried out during 2000 by softwood cuttings at a commercial nursery in New South Wales, Australia. 'VICLOW' has been found to retain its distinctive characteristics through successive asexual propagations. Multiple generations have been propagated, with the new variety characteristics reproduced true to type.

SUMMARY OF THE INVENTION

The following are the most outstanding and distinguishing characteristics of this new cultivar when grown under standard horticultural practices at New South Wales, Australia:

1. Short plants
2. Compact, bushy plants.
3. New growth leaf color near Greyed-Orange 166A.

COMPARISON WITH THE PARENT VARIETIES

'VICLOW' is distinguished from its female parent in the following:

1. The new variety produces greyed-orange new growth, whereas new growth of the parent variety is yellow-green.
2. Mature height of the new variety is significantly shorter than that of the seed parent.

COMMERCIAL COMPARISON

'VICLOW' is similar to the commercial variety *Acmena* 'Allyn Magic', unpatented, in most horticultural characteristics. 'VICLOW' however differs in the following:

1. Plants of the new variety produce a broad leaf, with an averge diameter of 39 mm, average leaf diameter of this comparator is 14 mm.
2. Leaf color of new growth of the new variety is greyed-orange 166A, of the comparator Greyed-Orange 177A.

DESCRIPTION OF THE PHOTOGRAPHS

This new *Acmena* is illustrated by the accompanying photographs which show the plant's form, foliage and inflorescences. The colors shown are as true as can be reasonably obtained by conventional photographic procedures. Plants were grown in New South Wales, Australia.

Figure 1:
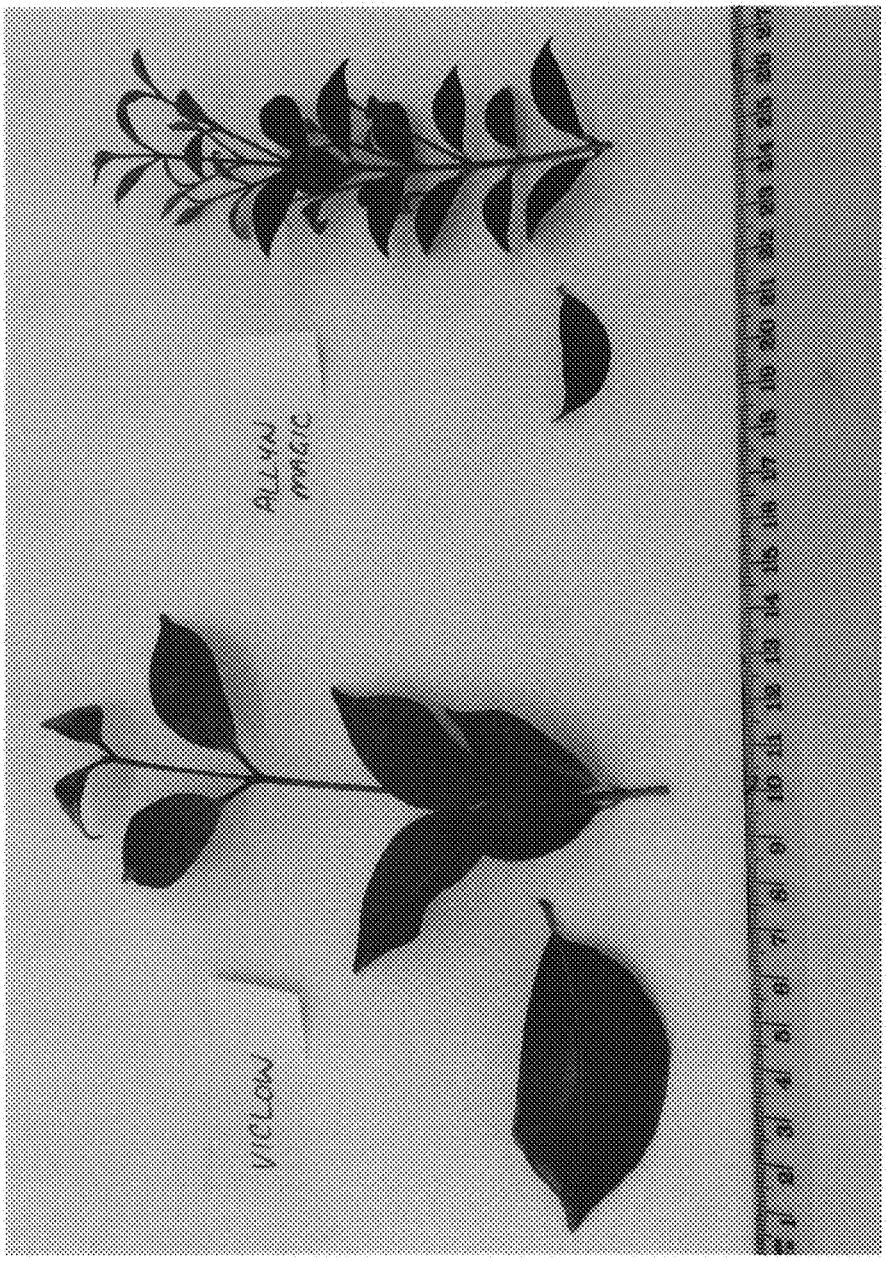

FIG. 1. Shows a foliage comparison of 'Viclow' with 'Allyn Magic', as well as new growth color.

Figure 2:
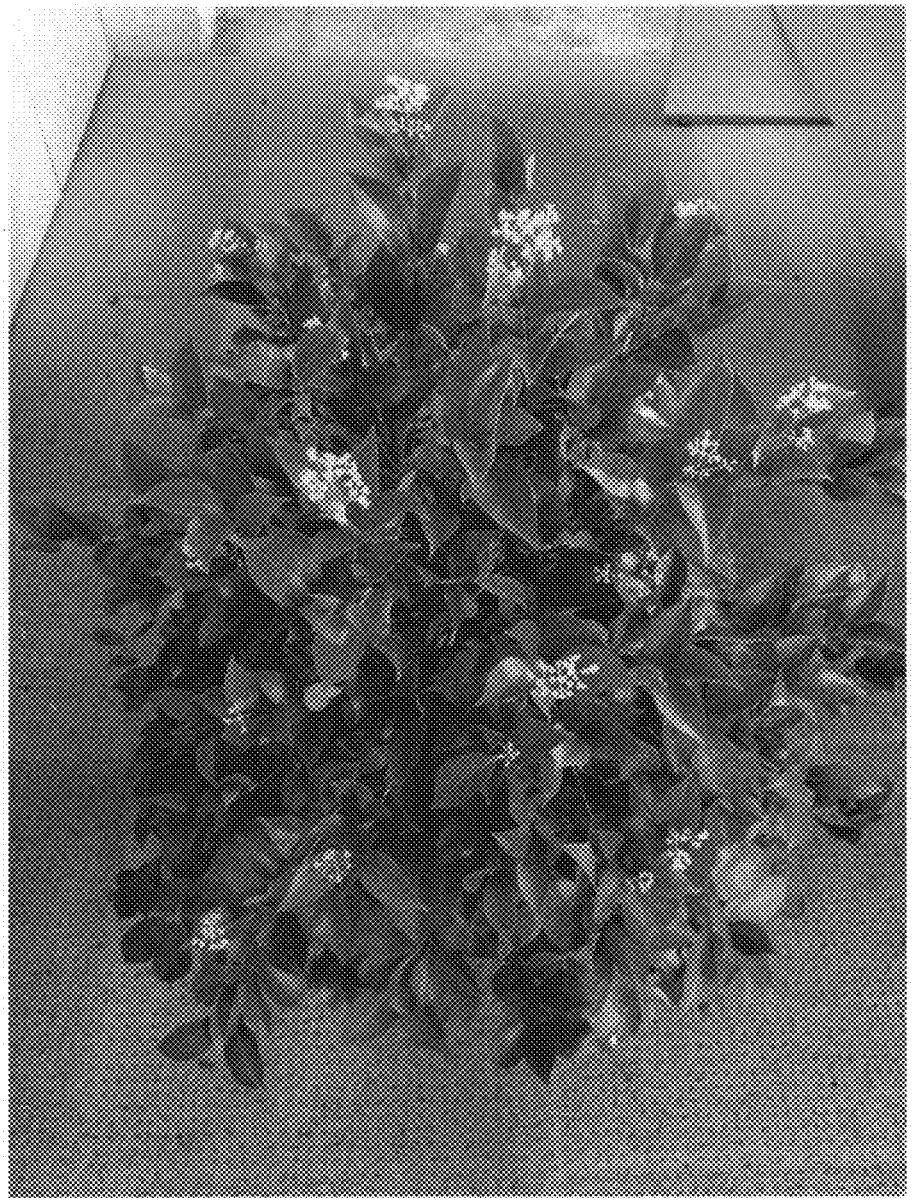

FIG. 2 depicts a plant of about 18 months in a 28 cm pot.

Figure 3:
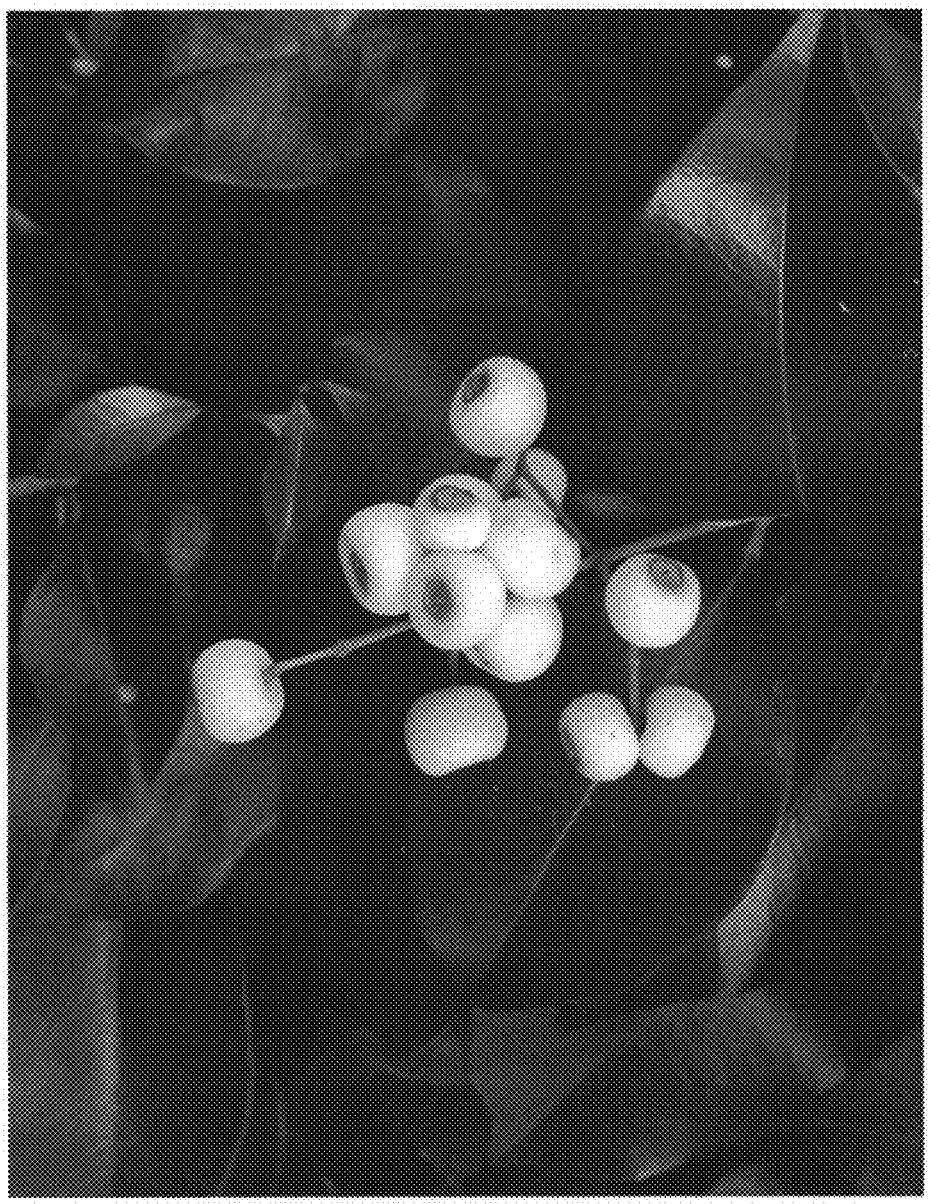

FIG. 3. Shows a close-up view of fruits.

Figure 4:
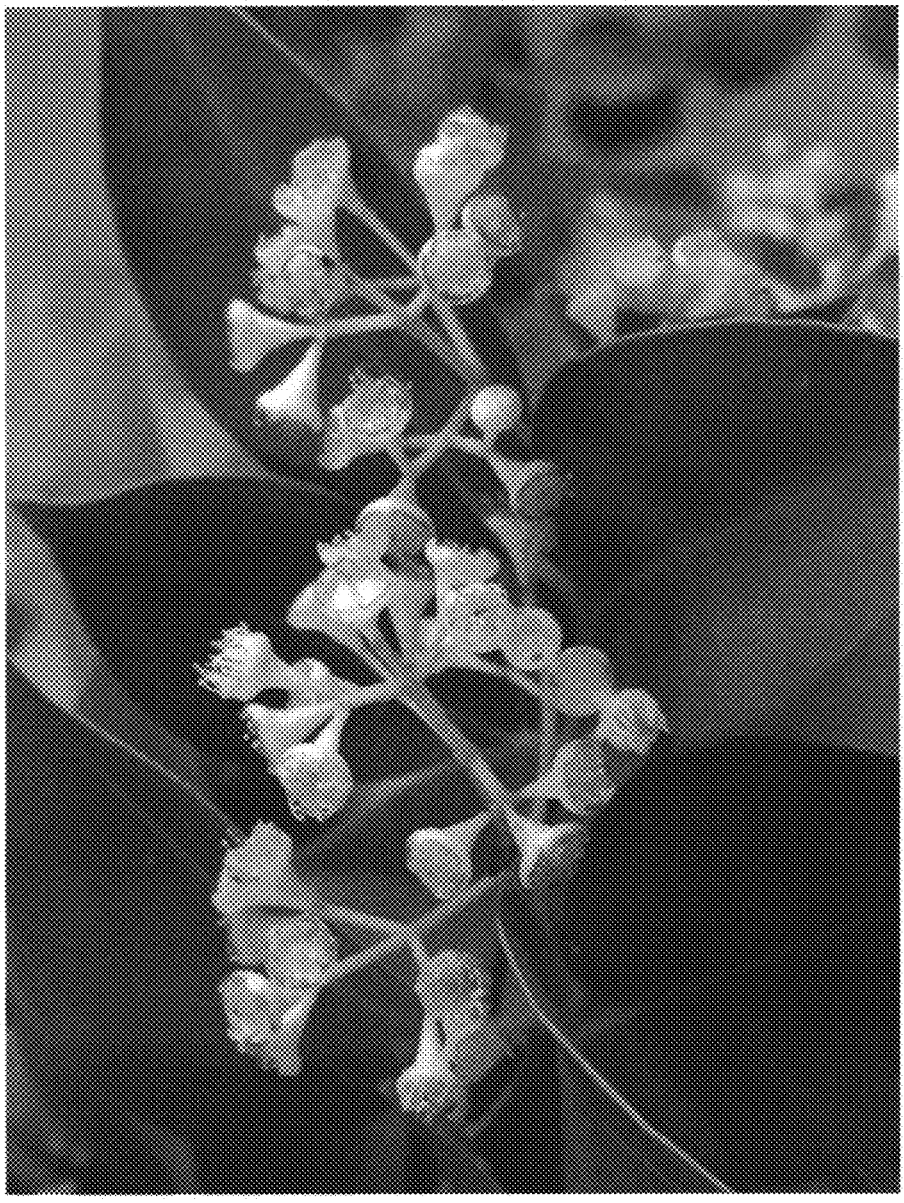

FIG. 4. Shows a close-up view of flowers, composed of a calyx and insignificant corolla.

DESCRIPTION OF THE NEW CULTIVAR

In the following description, color references are made to The Royal Horticultural Society Colour Chart 2015 except where general terms of ordinary dictionary significance are used. The following observations and measurements describe 'VICLOW' plants grown outdoors, in Kulnura, Australia. The growing temperature ranged from about 10° C. to 38° C. during the day and from 5° C. to 28° C. during the night. General light conditions are natural sunlight. Measurements and numerical values represent averages of typical plant types.

DETAILED BOTANICAL DESCRIPTION

Botanical classification: *Acmena smithii* 'VICLOW'.

Propagation:

Typical method: Softwood cuttings.

Time to initiate rooting: About 42 to 56 days at approximately 21° C.

Time to produce a rooted young plant: About 3 months at approximately 20° C.

Root description: Dense, somewhat free branching, fleshy roots of moderate thickness. Colored white, not accurately measured with an R.H.S. chart.

Plant description:

*Age of plant described.*—About 2 years in a 25 cm container.

*Growth habit.*—Perennial shrub. Spreading to bushy, with dense branching.

*Height.*—1.2 to 1.5 m.

*Width.*—1.5 to 2.0 m.

*Growth rate.*—Moderate.

*Typical commercial container sizes.*—1, 2 gallon.

Branches:

*Branching habit.*—Freely.

*Lateral branch quantity.*—Average range 10 to 15.

*Lateral branch length.*—Average range 20 to 30 cm.

*Lateral branch diameter.*—Average range 7 to 10 mm.

*Branch angle.*—Horizontal.

*Branch strength.*—Strong.

*Branch texture.*—Glabrous.

*Branch color.*—Mature Growth: Near Greyed-Green 199C. New Growth: Near Grey-Purple 183B.

*Internode length.*—20 to 25 mm.

Foliage:

Leaves:

*Persistence.*—Evergreen.

*Arrangement.*—Irregular alternate or whorled.

*Length.*—Avg. range 6.0 to 8.5 cm.

*Width.*—Avg. range 3.5 to 4.5 cm.

*Shape.*—Broad elliptic to slightly ovate.

*Apex.*—Acuminate.

*Base.*—Attenuate obtuse.

*Margin.*—Entire.

*Texture upper surface.*—Glabrous, glossy.

*Texture lower surface.*—Glabrous, slightly glossy.

*Color.*—Immature: Upper: Near Greyed-Orange 166A. Lower: Near Greyed-Orange 165A and 165B. Mature: Upper: Near Yellow-Green 146A. Lower: Near Yellow-Green 144B.

*Venation.*—Type: Pinnate, with a prominent midrib on lower side. Color: Upper: Near Yellow-Green N144B. Lower: Near Yellow-Green N144B.

*Petiole.*—Length: About 7.0 mm. Width: Average 2.0 mm. Texture: Glabrous. Color: New growth: Near Greyed-Yellow 160C. Mature: Near Greyed-Orange 165B.

*Durability.*—Very good durability to environmental stressors.

Inflorescence:

*Description.*—Terminal panicle.

*Flowering season.*—Spring to Summer.

*Fragrance.*—None.

*Inflorescence per branch.*—1 per branch, about 50 to 100 per plant.

*Number of flowers per inflorescence.*—About 15 to 30.

*Inflorescence height.*—Avg. 5.0 to 20.0 cm.

*Inflorescence diameter.*—Avg. 5.0 to 20.0 cm.

*Flowers.*—Flower diameter: 5 to 7 mm. Flower depth: about 5 mm. Flower Angle: Upright facing. Persistent of Self-Cleaning: Self-Cleaning.

*Flower bud.*—Length: 3 to 5 mm. Diameter: 2 to 5 mm. Shape: Orbicular. Color: Near RHS Yellow-Green 150D.

*Corolla.*—Insignificant, as typical to Genus. Less than 1 mm.

*Calyx.*—Length: 2 to 4 mm. Width: 2 to 4 mm. Shape: Conical. Texture: Glabrous inner and outer surfaces. Color: Yellow-Green 150D, inner and outer surfaces.

*Peduncle.*—Length: Average range 2 to 4 mm. Width: 1 mm. Color: Yellow-Green 150D. Texture: Glabrous. Angle: Upright. Strength: Strong.

*Pedicels.*—Length: Avg. 1 mm. Diameter: Avg. 1 mm. Texture: Glabrous. Color: Yellow-Green 150D. Strength: Strong.

Reproductive organs:

*Gynoecium.*—Pistil number: 1. Pistil length: 1 to 2 mm. Stigma shape: Linear. Stigma color: Yellow-green 150D. Style length: Less than 1 mm. Style color: White, not accurately measured with R.H.S. chart.

*Androecium.*—Stamen number: Numerous, highly reduced. Filament length: Less than 1 mm. Filament color: Yellow-Green 150D. Anther shape: Oblong. Anther length: Less than 0.5 mm. Anther color: Yellow-Green 150D. Amount of pollen: Moderate. Pollen color: Yellow 4B.

OTHER CHARACTERISTICS

Fruit: Globular, 10 mm long, 10 mm in diameter. Colored White N155B, calyx scar flushed Greyed-Purple 186A. Smooth texture.

Seed:

Disease and insect resistance: Good resistance to Myrtle rust (*Puccinia psidii*) has been observed. Good resistance to Psyllid (most likely *Acizzia uncatoides*) has been observed. No further significant disease or pest resistance nor susceptibility have been observed.

Cold hardiness: Observed to tolerate temperatures between −4° C. and 40° C.

What is claimed is:

1. A new and distinct *Acmena* plant named 'VICLOW' as illustrated and described herein.

* * * * *